United States Patent [19]
Jones

[11] Patent Number: 6,136,555
[45] Date of Patent: *Oct. 24, 2000

[54] PURIFICATION METHOD AND APPARATUS

[75] Inventor: Christopher Peter Jones, Herts, United Kingdom

[73] Assignee: Cambridge Molecular Technologies Limited, England, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/571,864
[22] PCT Filed: Jul. 8, 1994
[86] PCT No.: PCT/GB94/01484
    § 371 Date: Jan. 4, 1996
    § 102(e) Date: Jan. 4, 1996
[87] PCT Pub. No.: WO95/02049
    PCT Pub. Date: Jan. 19, 1995

[30] Foreign Application Priority Data

Jul. 9, 1993 [GB] United Kingdom .................. 9314249

[51] Int. Cl.[7] ............................... C12P 1/00; B01D 63/00
[52] U.S. Cl. .............................. 435/41; 435/259; 422/69; 422/101; 210/321.6; 210/321.64; 210/321.72
[58] Field of Search .................................. 68/12, 13, 18 F, 68/18 FA; 935/19, 20, 21; 435/6, 259, 810, 267, 268, 269, 270, 280, 173.1, 261, 91, 91.1, 89, 320.1, 287, 813, 41; 73/61.63, 863, 863.23; 536/124, 127, 128, 25.4, 25.41; 210/321.6, 321.64, 321.72; 422/69, 101

[56] References Cited

U.S. PATENT DOCUMENTS

| | | |
|---|---|---|
| 4,493,815 | 1/1985 | Fernwood et al. . |
| 4,895,706 | 1/1990 | Root et al. . |
| 4,997,932 | 3/1991 | Reardon et al. . |
| 5,273,718 | 12/1993 | Skold et al. . |
| 5,395,521 | 3/1995 | Jagadeeswaran ..................... 210/198.2 |

FOREIGN PATENT DOCUMENTS

| | | |
|---|---|---|
| 0268946A | 6/1988 | European Pat. Off. . |
| 0281390A | 9/1988 | European Pat. Off. . |
| 0366438A | 5/1990 | European Pat. Off. . |
| 0376080A | 7/1990 | European Pat. Off. . |
| 0389063A | 9/1990 | European Pat. Off. . |
| 0517515A | 12/1992 | European Pat. Off. . |
| WO 87/07645A | 6/1986 | WIPO . |
| WO 89/09265A | 3/1989 | WIPO . |
| WO 92/02303A | 7/1991 | WIPO . |
| WO 92/07863 | 10/1991 | WIPO . |
| WO 92/16294A | 2/1992 | WIPO . |
| WO 93/11218 | 12/1992 | WIPO . |
| WO 93/11221 | 12/1992 | WIPO . |

OTHER PUBLICATIONS

Somerville et al. "Simple, Rapid Method for Direct Isolation of Nucleic Acids from Aquatic Environment". Applied and Environmental Microbiology. vol. 55, No. 3, pp. 548–554, Mar. 1989.

Ji et al. "Rapid Purification of Double Stranded DNA by Triple–Helix Mediated Affinity Capture". Anal. Chem. vol. 65, pp. 1323–1328, 1993.

Stedman's Medical Dictionary, 24th Edition, Williams & Wilkins, Baltimore. 1982. p. 479.

*Primary Examiner*—Donna Wortman
*Attorney, Agent, or Firm*—Burns, Doane, Swecker & Mathis, L.L.P.

[57] ABSTRACT

A method is provided for purifying from cells a target compound such as nucleic acid. The method comprises the following steps: 1) lysing a cell suspension to form a cell lysate containing the target compound; 2) applying the cell lysate to a filter to remove unwanted cells and cell debris; 3) contacting the filtered lysate with a solid phase matrix under conditions to bind the nucleic acid to the matrix; 4) separating the resultant filtered lysate from the matrix; and 5) eluting the target compound from the matrix. Apparatus is also provided. Complex purification procedures such as centrifugation are avoided.

29 Claims, 5 Drawing Sheets

PURIFICATION METHOD AND APPARATUS

The present invention relates to a method and apparatus for purifying target compounds such as nucleic acids from cells.

Conventional procedures for the purification of protein or nucleic acid, such as DNA, require lysis of the source cells followed by various fractionation steps involving centrifugation. Where DNA manipulation is to be carried out, small scale DNA preparations are required routinely, often in large quantities for the purpose of screening the DNA from the source cells. These processes are time consuming and labour intensive.

It has been proposed to avoid centrifugation in the extraction and purification of DNA by a relatively complicated series of steps. EP 0376080 discloses in general terms the use of precipitants to precipitate DNA from accompanying impurities. Ultrafiltration is then used as a means to isolate the DNA. However, no worked example of the proposed process is described and no indication of its feasability is indicated. Ultrafiltration forms the basis of other DNA purification methods as described in WO 87/07645 and EP 0517515.

Cation exchange resins have also been proposed as a means for separating relatively uncontaminated nucleic acids from impurities. EP 0281390 discloses the use of polycationic solid supports particularly to separate hybridized from unhybridized nucleic acids. EP 0366438 discloses the separation of nucleic acid from protein by binding the protein to a cation exchange resin.

A partially automated apparatus for carrying out biochemical reactions is disclosed in WO 92/02303 in which mountings for manipulating microtiter plates are proposed.

The present invention aims to provide an improved method for the purification from cells of target compounds such as nucleic acids, which method avoids the use of centrifugation, ultrafiltration or other complex procedures.

The target compound may comprise nucleic acid, protein or other desired compounds and is produced by the cell and expressed either internally or externally. Apart from nucleic acids, the method is particularly attractive for purifying recombinant proteins and antibodies.

In one aspect, the present invention provides a method for purifying nucleic acid from cells. The method comprises the following steps:

(1) lysing a cell suspension to form a cell lysate containing nucleic acid;
(2) applying the cell lysate to a filter to remove unwanted cells and cell debris;
(3) contacting the filtered lysate with a solid phase matrix under conditions to bind the nucleic acid to the matrix;
(4) separating the resultant filtered lysate from the matrix; and
(5) eluting the nucleic acid from the matrix.

Because the method of the present invention is relatively simple, starting with the cell suspension it can be applied as a continuous method (i.e. without interruption from batch of cell suspension to desired product), for example in automated apparatus.

In a further aspect, the present invention provides a continuous method for purifying a target compound from cells. The method comprises the following steps:

(1) obtaining a cell suspension containing the target compound;
(2) applying the suspension to a filter to remove unwanted cells and cell debris;
(3) contacting the filtrate with a solid phase matrix under conditions to bind the target compound to the matrix;
(4) separating the resultant filtrate from the matrix; and
(5) eluting the target compound from the matrix.

Preferably, the cell suspension is lysed in step (1) to form a cell lysate containing the target compound.

Preferably, the method further comprises the step of washing the matrix binding the target compound so as to remove contaminants before eluting the target compound from the matrix.

Any cell producing the target compound may be used in the method. For the purpose of this specification, the term "cell" is intended to encompass bacterial cells, cells from higher organisms, phage particles and other cell types or organelles which contain the target compound and may require some form of lysis step to release it. In the case of bacteria, nucleic acid may come from the bacterial nucleus or from cellular inclusions such as plasmids. Indeed, the method is especially useful for the preparation of plasmid DNA. Phage-infected bacteria may also be used in the preparation of phage DNA, such as M13 DNA. Cells from higher organisms include blood cells. Where genomic nucleic acid is to be prepared, nucleated blood cells form the cell suspension for lysis.

As a typical first step in the method, a cell suspension is formed by applying a cell culture to the filter so as to separate the cells from the culture medium. The liquid medium passes through the filter and is discarded. The cells on the filter are resuspended in a suitable resuspension buffer ready for lysis. However, in the case of phage, depending on the type of phage, it may be necessary to introduce an extra filtration step so as to clear phage cells (particles) from the cell debris. For example, where lambda phage infects bacteria, some infected bacteria lyse and some do not. In this case, it is necessary to use the extra filtration step as a pretreatment. In the pretreatment, the initial mixture of lysed bacterial cells, unlysed bacterial cells and unlysed phage cells (particles) is typically filtered through a pretreatment filter to remove unlysed bacterial cells and cell debris. The resultant phage cells are then kept in suspension ready for lysis, along the lines described below. Preferably, the suspension of phage cells is concentrated before lysis. Concentration may be effected by treatment with salt and a hydrophobic agent such as polyethylene glycol (PEG). In contrast, where phage M13 infects bacteria, no lysis of the bacterial cells occurs and so no extra filtration step is required.

The step of lysing the cell suspension typically requires the addition of a further aliquot of lysis buffer. After lysis, it is sometimes preferable to add a neutralization solution to the lysed cell suspension. Typically, the buffers for resuspension and lysis and the neutralization solution are all well-known in this field and can vary according to the cell type and target compound to be purified. For example, where nucleic acid is to be purified the resuspension buffer typically contains a chelating agent to remove metal ions from the medium and may a have pH in the range 7 to 8.5, advantageously in the range 7 to 8. For plasmid purification the lysis buffer is typically alkaline and includes a surfactant such as sodium dodecylsulphate (SDS). The neutralization solution is intended to bring the pH back into a useful range and can flocculate unwanted protein and is typically a highly concentrated salt solution such as potassium acetate at around 2.5 M. For nucleic acid purification from blood cells, the lysis buffer includes NonIdet P-40 as a typical surfactant and the pH is preferably raised to around pH 8.3.

The nucleic acid may be DNA or RNA. Where DNA is to be purified, the resuspension buffer may contain RNase to cleave unwanted RNA. Where RNA is to be purified the resuspension buffer may contain DNase to cleave unwanted DNA. Optionally, for nucleic acid purification the resuspension buffer may also contain proteases, for example proteinase K.

At each stage of adding the resuspension buffer, lysis buffer, and neutralization solution, it is preferable to mix the solutions well together.

After lysis, the cell lysate is applied to the filter to remove unwanted cells and cell debris thereby giving rise to a crude preparation of the target compound and other soluble contaminants. Any filter commonly available may be used in this step provided that the filter can tolerate the reagents being used and provided that the unwanted cells and cell debris are retained by the filter. For example, the filter may be made of cellulose acetate, PTFE, or any other similar material. Preferably, the pore size of the filter is no greater than 50 microns. Too large a pore size lets through unwanted matter. If the pore size is reduced below 0.2 microns the flow rate through the filter is disadvantageously low. In practice, the pore size is chosen in accordance with the cell density and nominal cell size.

The solid phase matrix used in the present method must bind the target compound under the operating conditions used. The operating conditions must therefore be tailored in accordance with the type of matrix and the target compound. For nucleic acid, the matrix is typically glass- or resin-based and can bind the nucleic acid by ionic interaction, affinity interaction or hydrophobic interaction. Advantageously an ion exchange material is used, preferably an ion exchange resin commercially available for this purpose. Cation exchangers are preferred ion exchangers on the basis that, at typical working pHs, the target nucleic acid is negatively charged. Possible cation exchangers include any suitable proprietary resins (such as the "Magic" or "Wizard" range from Promega Corp. or Sephacryl from Pharmacia AB) or borosilicate glass exchangers or diatomaceous earth. As a further option, a poly-adenylene column may be used.

In each case, the conditions of pH and salt concentration will affect both the ability of the target compound and the unwanted contaminants to bind to the matrix. It is therefore advantageous to include the step of washing the matrix prior to elution so as to remove unwanted contaminants which bind less strongly to the matrix than the target compound. A typical wash buffer for nucleic acid is alcoholic Tris-HCl at around pH 7.5 with 200 mM sodium chloride and 5mM EDTA.

The contacting of the filtrate with the solid phase matrix may occur simply by passing the filtrate through a volume of the matrix, perhaps in the form of a column, for example. Alternatively, a suspension of the matrix may be added to the filtrate. Separation of the thus-treated resultant filtrate from the matrix may be effected simply by retaining the matrix and discarding the unwanted liquid phase.

Elution of the target compound from the matrix will depend upon the nature of the interaction between the compound and the matrix. Where ionic interactions predominate, it is usual to elute the nucleic acid in an elution buffer having lower salt concentration. Higher pH or higher salt is generally required for proteins. Alternatively, the elution buffer may contain an affinant designed specifically to elute the target nucleic acid or protein.

It is generally advantageous to keep the target compound in solution when not bound to the solid phase matrix. The method is therefore preferably carried out substantially in the absence of any precipitation of the target compound.

In contrast to the general methodologies described above, where the target compound to be purified is M13 DNA a modified method is preferred. In this case, the source "cells" comprise M13 phage particles. Bacterial cells infected with the M13 phage are filtered to remove unwanted bacterial cells and bacterial cell debris so that the filtrate contains the M13 phage particles. The phage particles are precipitated with any suitable precipitant, such as glacial acetate acid and subsequently lysed by contact with a suitable chaotropic lysis solution such as concentrated $NaClO_4$. The lysed M13 phage particles now present in the filtrate are contacted with a solid phase matrix suitable for binding the phage DNA. The matrix may be contacted as described above or, in a convenient embodiment, may be present in the form of a filter to which the lysed phage particles bind such as a borosilicate glass filter. The matrix is advantageously washed with a suitable washing solution, such as an ethanol solution, and the DNA eluted as described above.

In a further aspect of the present invention apparatus is provided for purifying a target compound from a cell suspension. The target compound may be a target macromolecule such as protein or nucleic acid, preferably a nucleic acid. The apparatus comprises a first chamber to receive the cell suspension;

a filter downstream of the first chamber for retaining unlysed cells and cell debris; and a second chamber to receive filtrate downstream of the filter and communicating with means for delivering solutions thereto;

wherein means are provided in or downstream of the second chamber for retaining a solid phase matrix to bind the target compound and an outlet for delivering the purified target compound is provided downstream of the means for retaining the solid phase matrix.

Preferably, the first chamber communicates with further means for delivering solutions thereto.

The apparatus can be incorporated into an automatic system comprising one or more apparatus arrangements as described, together with a central control means for controlling the apparatus. The apparatus is particularly suitable for operating the method described above and can, in automated form, permit the simultaneous operation of a plurality of separate purifications in a routine manner.

Each means for delivering solutions to the respective chambers may comprise any suitable device for liquid delivery. For example, a syringe may be provided for the delivery of each buffer solution. Alternatively, a plurality of reservoirs containing the appropriate reagents may be connected by valves to each chamber, for example through a common port. In the automatic version of the apparatus the control means would be linked to the valves to ensure delivery of the correct sequence of solutions.

In a preferred embodiment, the apparatus further comprises first pressurization means for providing a positive pressure at the upstream end of the filter relative to the downstream end thereof. The purpose of the pressurization means is to force or draw liquid in the first chamber through the filter so as to separate the liquid from cells or cell debris which are retained on the filter. This may be effected by applying positive pressure upstream of the filter, for example by using the means for delivering the solutions to the first chamber to create positive pressure in the first chamber. In a further arrangement, the pressure is lowered at the downstream end of the filter, for example by using a vacuum line. In a still further arrangement, a syringe or similar means may reduce the pressure at the downstream end of the filter and, at the same time, collect waste wash buffer.

Preferably, the means for retaining the solid phase matrix comprises a barrier to the solid phase matrix which is advantageously situated between at least a part of the second chamber and the outlet. In this arrangement, it is convenient for the solid phase matrix to be held at the end of the second chamber downstream from the filtrate and permit discarded solutions to pass through the matrix and the barrier and to exit from the apparatus at the outlet. In an alternative arrangement, the outlet may be provided above the level of the barrier. In a further embodiment of the apparatus, the apparatus can be supplied with the solid phase matrix already in position. The barrier is preferably a filter of the type described above. PTFE is a particularly useful material for this filter.

As an alternative, the barrier need not be a separate component but may instead arise simply from the geometry of the second chamber, for example as a wall or compartment thereof.

In analogous fashion to the first pressurization means, the apparatus may further comprise a second pressurization means for providing a positive pressure at the upstream end of the barrier relative to the downstream end thereof. As discussed in relation to the first pressurization means, either positive pressure at the upstream end of the barrier or negative pressure at the downstream end of the barrier may be applied. In one embodiment, a separate waste outlet is provided in addition to the outlet for the purified target compound. Negative pressure may be applied to the waste outlet, for example using a vacuum line for the purpose of removing unwanted liquids from the solid phase matrix.

Each of the outlets may be valve controlled and in the automatic version of the apparatus, the valves would be linked to the control means.

Advantageously, the means for delivering solution and, when present, the means for delivering suspensions and the pressurization means are driven by a pneumatic fluid delivery system using continuous pressure, preferably continuous positive pressure.

Where phage-infected bacteria are used as the source material and lysed and unlysed bacterial cells are formed, a further embodiment of the apparatus may be required. In this embodiment the apparatus further comprises a pretreatment chamber upstream of the first chamber to receive lysed and unlysed bacterial cells infected with phage and a pretreatment filter, downstream of the pretreatment chamber and upstream of the first chamber, for retaining unlysed bacterial cells and bacterial cell debris.

In a preferred embodiment, a single column arrangement is used in which the filter acts to partition the first chamber from the second chamber. In this type of arrangement the wall or walls defining the first chamber are continuous with those defining the second chamber. This has the advantage that the arrangement can withstand relatively high operating pressures such as those used in pneumatic delivery systems of the type described herein. In a further embodiment, the first and second chambers are positioned side-by-side and the (vertical) filter again acts as a partition between the chambers. It is also possible to have the two chambers intercommunicating by means of tubing with in-line filters separate from the chambers.

In a particularly preferred embodiment, the apparatus is provided with fluid delivery means having an outlet which is positioned to communicate with liquid when present in the second chamber. Typically, the liquid collects at the bottom of the second chamber and the outlet is positioned below the surface of the liquid. Whilst the fluid delivery means could act as the second pressurization means, it is preferably separate from the second pressurization means and capable of delivering both liquid and gas to the second chamber. The positioning of the outlet enables gas to pass directly into the liquid in the second chamber so as to facilitate mixing of the components of the liquid. This is particularly useful where a suspension or slurry of solid phase matrix is supplied to filtered lysate in the second chamber. Gas expelled from the outlet facilitates mixing of the solid phase matrix with the filtered lysate to maximise contact of the target compound with the matrix.

The present invention will now be described further, by way of example only, with reference to the accompanying drawings, in which:

Figure 1:
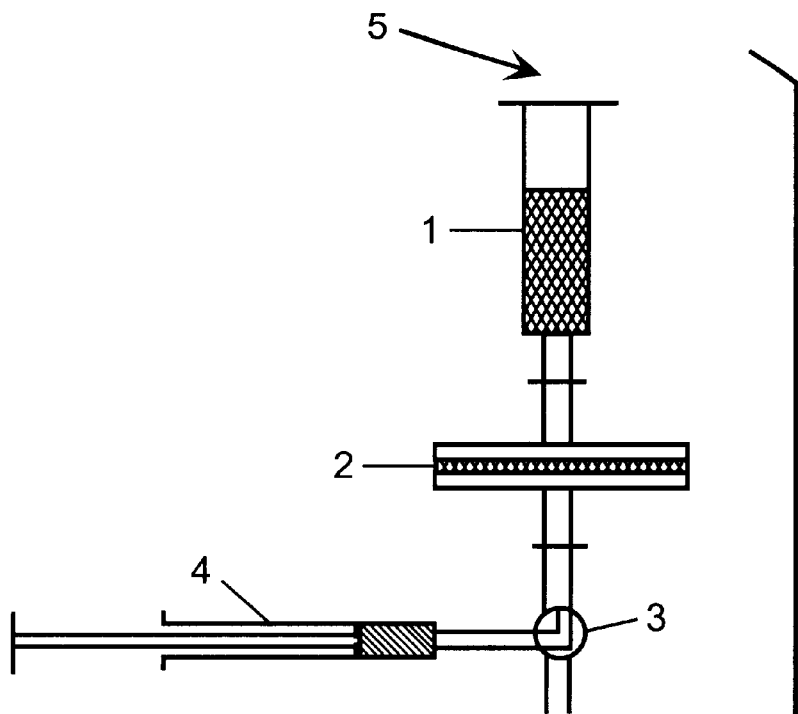
FIG. 1 shows a simple manually-operated apparatus according to the present invention for plasmid DNA.
Figure 1:
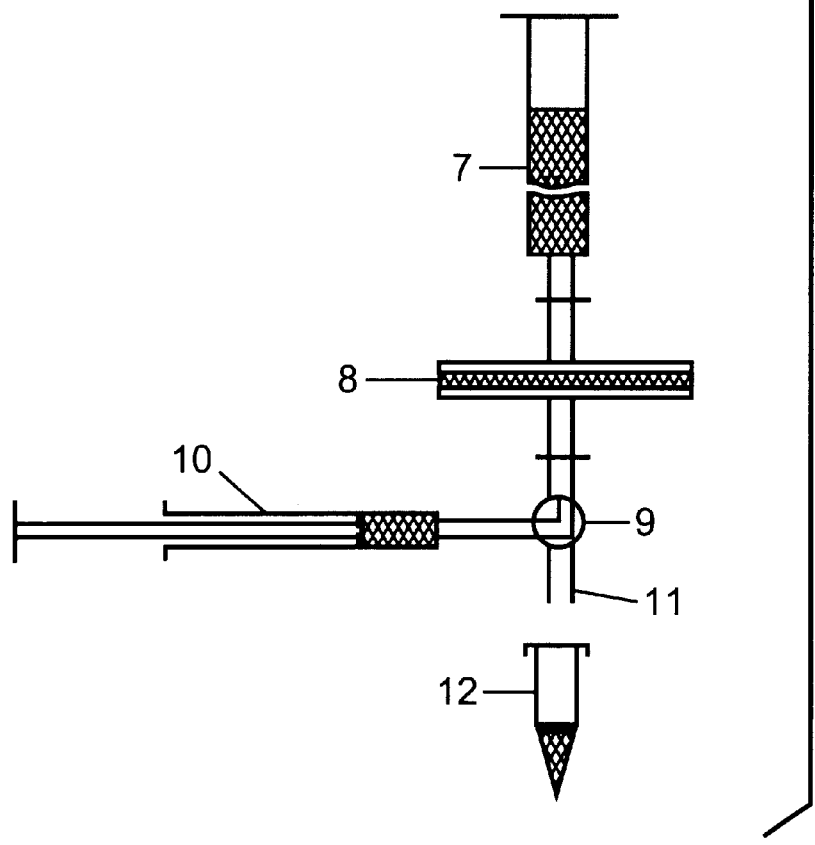

In the simple embodiment of the invention shown in FIG. 1, cell reservoir 1 communicates with filtrate reservoir 7 through filter 2 and three-way valve 3. Similarly, filtrate reservoir 7 communicates with outlet 11 through filter 8 and three-way valve 9. Syringes 4 and 10 are also connected respectively to three-way valves 3 and 9. Collection tube 12 communicates with outlet 11 to collect the purified sample.

Figure 2:
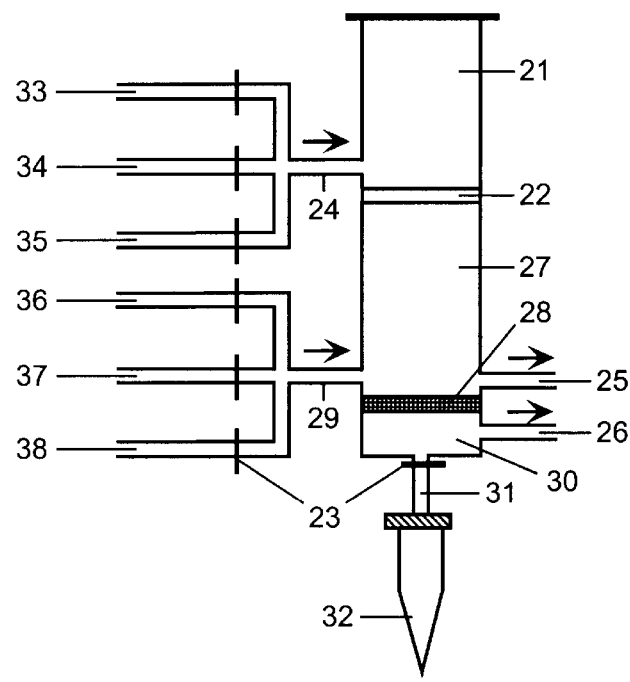
FIG. 2 shows a column version of the apparatus.

In the column embodiment of the invention shown in FIG. 2, the two chambers 21 and 27 are partitioned by filter 22. Further filter 28 acts as a barrier to prevent solid phase matrix in chamber 27 from passing to the remainder of the second chamber 30 and to the outlet 31. In order to deliver solutions to the chambers 21 and 27, reagents from reservoirs (not shown) enter at inlets 33 to 38. The inlets are all controlled by valves 23. Common ports 24 and 29 connect the reagent reservoirs with chambers 21 and 27 respectively. Vacuum lines can be applied to conduits 25 and 26. Conduits 25 and 26 act additionally as waste outlets. Collection tube 32 communicates with outlet 31 to collect the purified sample.

Figure 3:
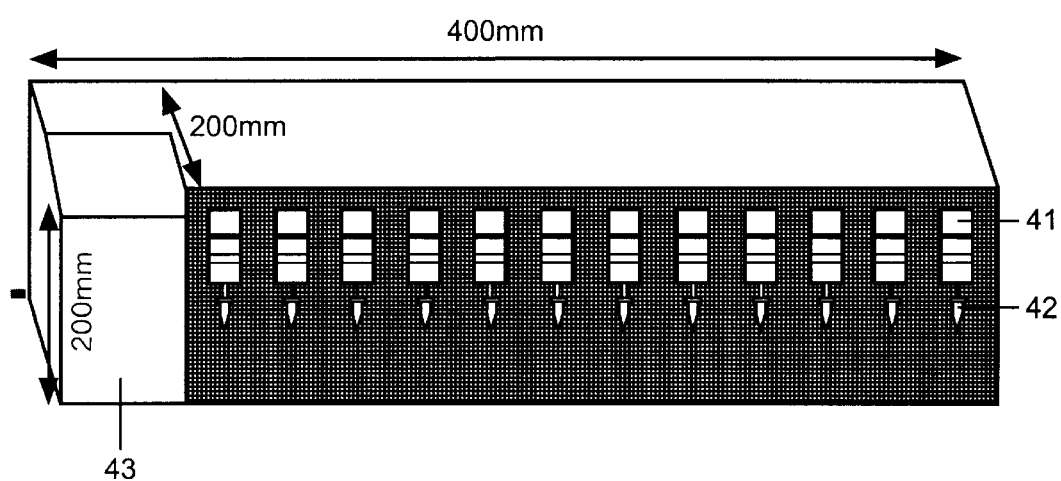
FIG. 3 shows an automated version of the apparatus.

A plurality of the columns can be assembled in the arrangement in FIG. 3. Columns 41 and collection tubes 42 are shown. A reagent, fluid delivery and control system 43 is present to control the process in each column.

Figure 5:
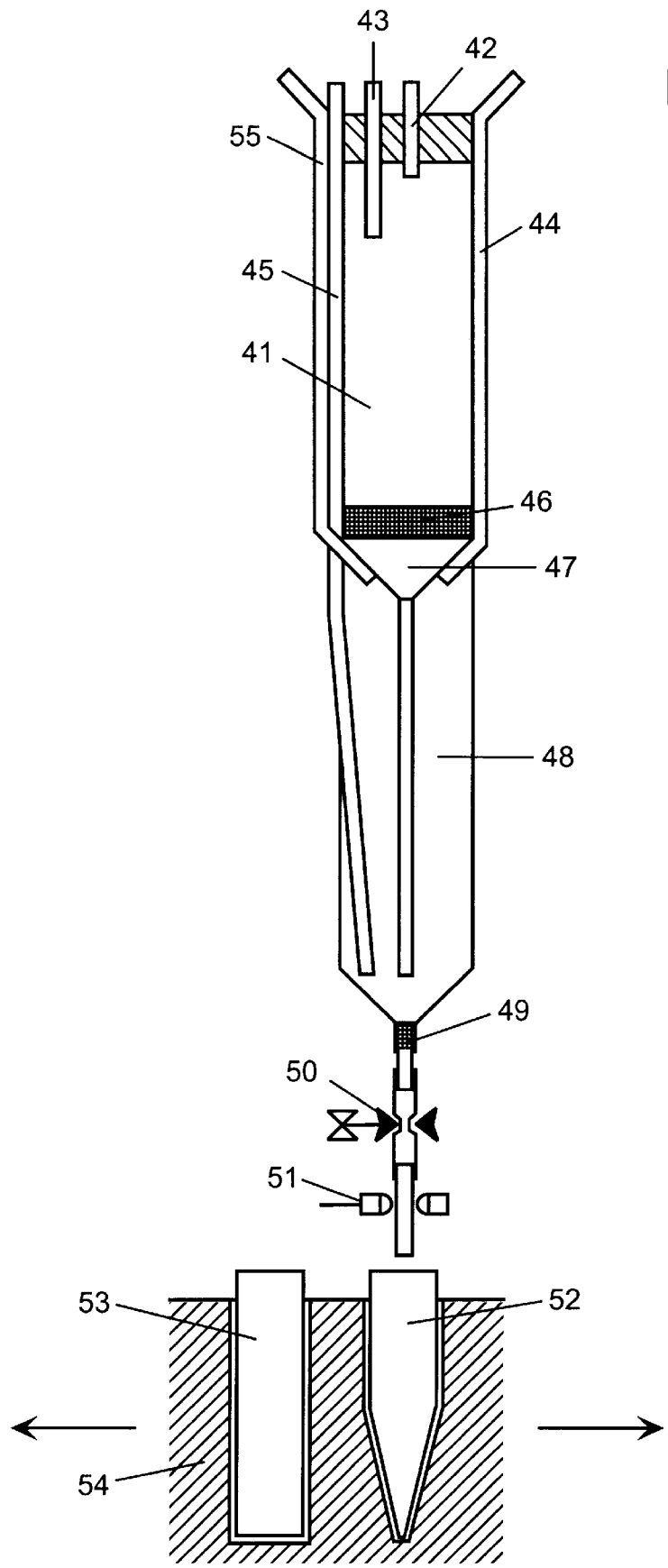
FIG. 5 shows a second column version of the apparatus.
Figure 6:
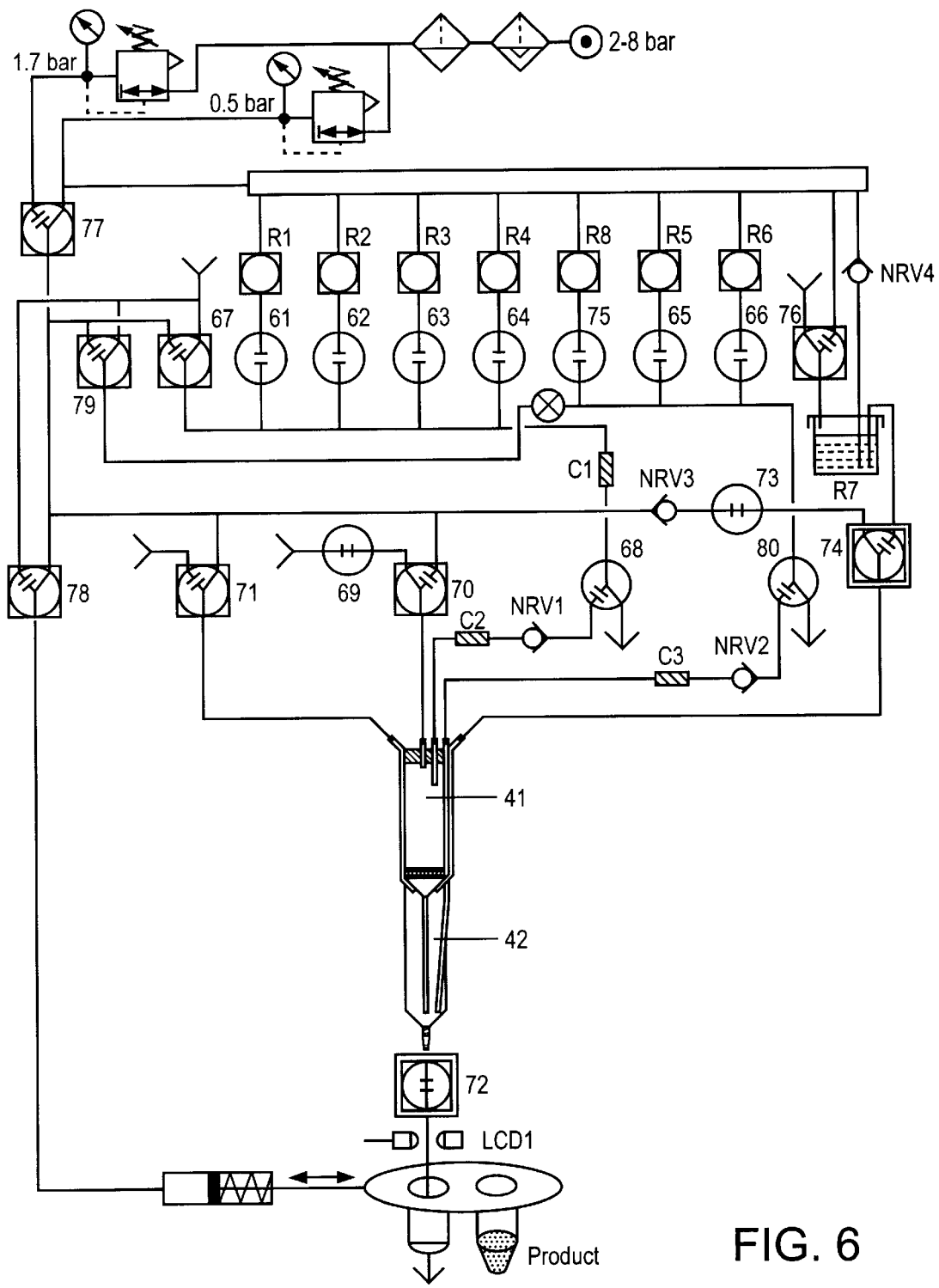
FIG. 6 shows a circuit diagram for operation of the apparatus.

The second column embodiment of the invention shown in FIG. 5 can be used in accordance with the circuit shown in FIG. 6.

Referring to FIG. 5, the two chambers 41 and 48 are partitioned by filter 49. Further filter 48 acts as a barrier to prevent solid phase matrix in chamber 48 from passing out of the column. Inlet 42 is provided in the first chamber of the column for the passage of pressurised air and also to allow air to be vented from the column. Inlet 43 is provided for the addition of liquids to the column. Conduit 47 consists of a conical portion connected to a tubular portion. Conduit 47 collects liquid from filter 46 and transfers the liquid to a collection point typically at the base of the second chamber 48. The base of the second chamber includes a conical recess to maximise liquid collection at the low volumes typically used in the apparatus. Line 44 is provided at the top of the second chamber for passage of pressurized air into the column and also to allow air to be vented from the column. A further inlet 45 is present for the addition of liquids or gas to the column and consists of a tube with an outlet located near to the bottom of the column. Pinch valve 50 is situated downstream of filter 49 to control flow from the second chamber and is monitored by means of liquid sensor 51. Indexing mechanism 54 controls the relative position of waste tube 53 or collection tube 52 according to whether liquid flowing from the column is intended for sampling or to be disposed of.

The liquid delivery system shown in FIG. 6 comprises a number of reagents in reservoirs (R1 to R8) which are pressurized typically at 0.5 bar fine pressure regulated air. The exact number of reagents used will depend on the exact purification protocol to be adopted. The reagents are divided into two blocks: reservoirs R1 to R4 contain reagents to be delivered to inlet 43 of the column and are controlled by corresponding valves 61 to 64; and reservoirs R5, R6 and R8 contain reagents to be delivered to the second chamber of the column through inlet 45 under control of valves 65 and 66. Reservoir R7 contains particulate matrix material to be delivered by an independent line to the top of chamber 48 through inlet 55 under control of corresponding valves 74 and 76.

Taking delivery of reagent from reservoir R4 as an example, this reagent is delivered by opening valve 64 for a selected time period (e.g. 250 ms). Because the reservoir is under pressure and there is a drop in pressure on the open side of valve 64, reagent enters the system until the valve closes. There is now a volume of liquid in the line from valve 64 to valve 68. The length and diameter of this line is chosen to accommodate the maximum likely volume. The volume of reagent is then moved to the top of the first chamber by switching valve 68 on and switching valve 67 on for sufficient time to allow the reagent to reach the top of the chamber. The pressure of the air forcing the liquid down the line can be either 0.5 bar or, if valve 77 is switched on, 1.7 bar. The air in front of the liquid to be moved is vented to atmosphere via valves 69 and 70. All valve timings are controlled by a microprocessor (not shown).

Liquid flow to the column is controlled by flow constrictors C1 to C3 (0.3 mm) or by using small diameter lines (0.5 mm or less—say valve 80 to non-return valve NRV2). Non-return valves NRV1 to 4 are also incorporated in various parts of the circuit to prevent reverse flow.

By analogy with the delivery of reagent from reservoir R4, a similar arrangement of valve control is used for delivery of reagent from reservoirs R2, R3, R5 and R6. In order to wash the lines after addition of reagents from the reservoirs R2, R3 and R4 a volume of water is flushed through the lines from reservoir R1 in a similar manner as the delivery of reagent but the water is diverted to waste at valve 68. A similar function is performed for washing the lines from reservoirs R5 and R6 using water in R8 diverted to waste via valve 80.

Because of the particulate nature of the solid phase matrix reagent in reservoir R7, a separate delivery system is provided. This reagent is enclosed within a sealed reservoir and two lines go into the reagent while another is located at the top of the reservoir. In order to mix the matrix prior to delivery and to ensure that it is in suspension, valve 76 is opened to allow air to escape via the vent. Because the reservoir is sealed to form a closed system, air is drawn in via non-return valve NRV4 resulting in a bubbling action sufficient to suspend matrix particles in the reagent. Valve 76 is then closed and an appropriate dose of the reagent from reservoir 7 is removed by opening pinch valve 74. The reagent is delivered to the top of the second chamber of the column by opening valve 73 and venting via valve 71.

Where the transfer of liquid in the column from first chamber 41 to second chamber 48 is required, this is achieved by closing valves 68, 73 and 72 and allowing air to enter the top of the first chamber via valve 70. Any liquid in the first chamber is transferred to the second chamber with air being vented via valve 71. Sensor 51 provided at the column outlet assesses whether liquid has passed out of the column via valve 72. Indexing mechanism 54 is provided to move collection tube 52 into position to receive the product of the purification system.

EXAMPLE 1

In this Example the following materials were used.

| Buffer (volumn/prep) | Composition |
| --- | --- |
| Resuspension Buffer (300 ul) | 50 mM Tris-HCl pH 7.5 10 mM Ethylenediamine tetra acetic acid (EDTA) 100 g/ml RNase A |
| Lysis Buffer (300 ul) | 0.2 M NaOH, 1% Sodium dodecylsulphate |
| Neutralising Solution (300 ul) | 2.55 M Potassium acetate |
| Matrix (500 ul) | Wizard (formerly Magic) Minipreps DNA purification resin in 7 M Guanidine hydrochloride Wizard and Magic Minipreps are registered trade marks of Promega Corp. |
| Wash Buffer (2000 ul) | 200 mM Sodium chloride 20 mM Tris-HCl, pH 7.5 5 mM EDTA 50% ethanol |
| Elution Buffer (50 ul) | 10 mM Tris-HCl, pH 7.5 1 mM EDTA |

Referring to FIG. 1, a bacterial cell culture containing plasmid DNA was added to the cell reservoir 1 at a volume of 2 ml. The culture was filtered through filter 2 (8 micron cellulose acetate) via three-way valve 3 by means of a vacuum created by withdrawing the barrel of syringe 4 and collecting filtrate in syringe 4. The cells were left on the surface of the filter 2. Syringe 4 was disconnected, the filtrate discarded and the syringe 4 was repositioned on three-way valve 3. Through the opening 5 successive additions of cell resuspension buffer, cell lysis buffer and cell neutralization solution were made. Between each successive addition the cells were mixed by plunging syringe 4 to provide plenty of turbulence. After the final addition, the entire liquid phase was filtered through the filter 2 and collected in syringe 4. A solution of crude DNA was thus prepared.

Three-way valve 3 was then turned so that the entire contents of syringe 4 could communicate with filtrate reservoir 7. The contents of syringe 4 were then expelled into the filtrate reservoir 7 to which was added the matrix suspension. The crude DNA and matrix were mixed by moving syringe 10 in and out at a distance equivalent to the void volume of the matrix. The entire contents of the filtrate reservoir 7 were then filtered through filter 8 (sintered PTFE) using syringe 10 to create a vacuum. Three-way valve 9 was then switched so that the filtrate could be discarded. Wash buffer was added to the filtrate reservoir and voided as previously discussed. All residual wash buffer was removed by passing air through the filter 8 by means of plunger syringe 10. Finally, elution buffer was added to the filtrate reservoir 7, mixed by use of the syringe 10 and passed through filter 8. The purified DNA was separated from the resin in the elution buffer and collected in collection tube 12 by switching three-way valve 9.

Figure 4:
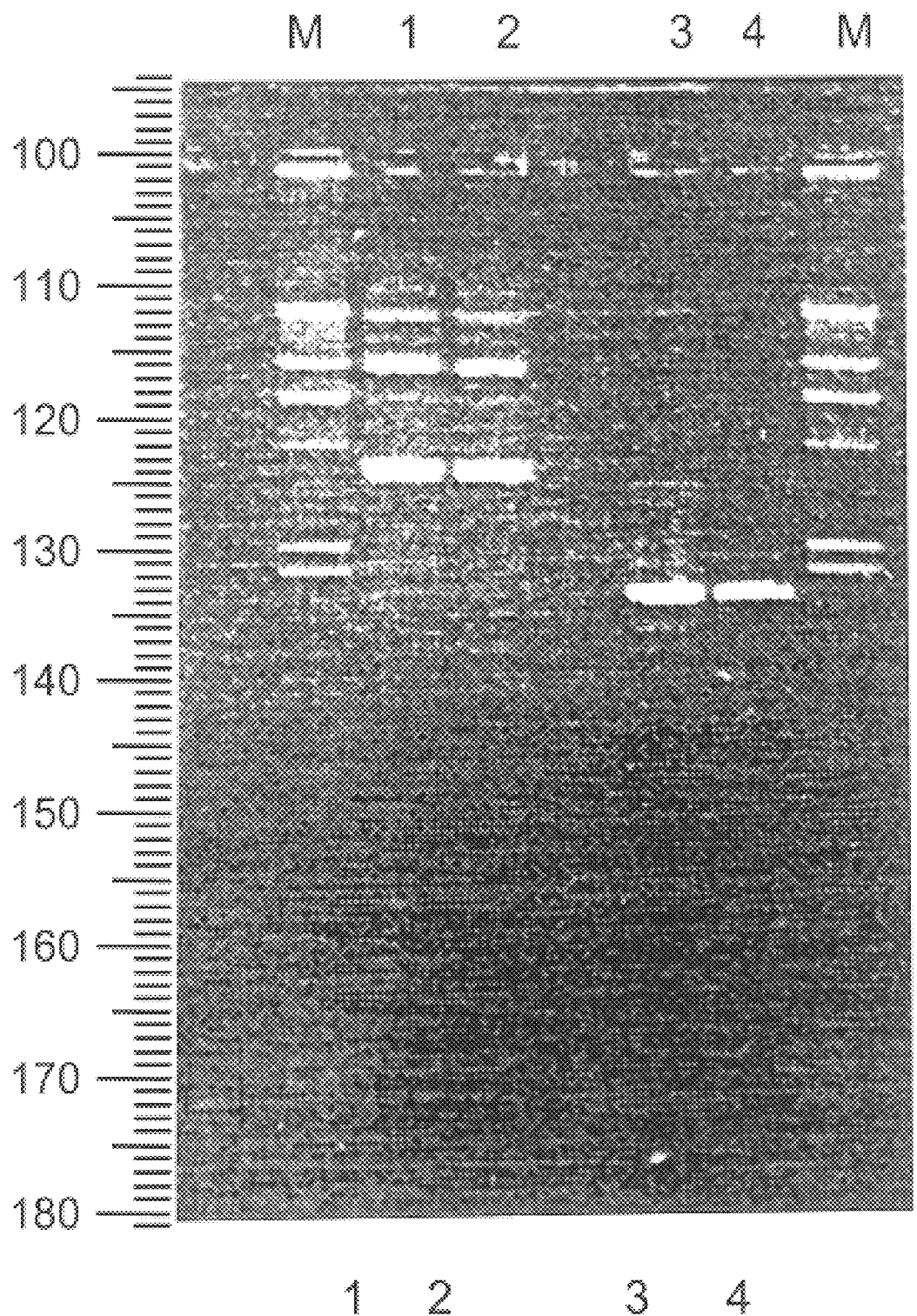
FIG. 4 shows the results of agarose gel electrophoresis comparing DNA samples prepared conventionally and samples in accordance with the present invention.

The results of the present Example are shown in FIG. 4 as a comparison with results obtained using conventional centrifugation techniques. For both methods a starter culture of 5 ml plasmid-containing E. coli K12 DH5 alpha was grown and 2 ml of the culture was used to prepare plasmid DNA. Two separate cultures were prepared by each method: one containing plasmid pBS SKII+; and one containing a clone of pBS SKII+containing insert pFB41B2.

The results are shown in FIG. 4 in accordance with the following key.

| Lane | Sample |
|---|---|
| M | MW marker lambda/Hind III |
| 1 | pBS SKII+/pFB41B2 (Example) |
| 2 | pBS SKII+/pFB41B2 (conventional) |
| 3 | pBS SKII+ (Example) |
| 4 | pBS SKII+ (conventional) |
| M | MW marker lambda/Hind III |

It will be appreciated from FIG. 4 that the yield from the present invention is comparable if not slightly greater than that obtained by conventional centrifugation Moreover, the purity of the DNA preparations according to the present invention is at least comparable to those prepared by conventional methods. For example, DNA prepared according to the present invention is ready for restriction enzyme analysis and manipulation without the need to undergo further purification steps.

EXAMPLES II to IV

In these Examples the materials were used as shown in Table I.

TABLE 1

| | Composition of reagents for DNA purification Examples II–IV | | |
|---|---|---|---|
| Reagents | Example II Plasmid | III M13 | IV Blood |
| 1 | de ionised water | de ionised water | de ionised water |
| 2 | 50 mM Tris-HCl pH 7.5 10 mM EDTA 10 μg/ml RNAase A | Glacial acetic acid | PBS |
| 3 | 0.2 M NaOH 1% SDS | 4 M NaClO$_4$ | 20 mM Tris-HCl pH 8.0 5 mM EDTA pH 8.0 |
| 4 | 2.55 M Potassium acetate | 70% Ethanol | 50 mM KCl 10 mM Tris-HCl pH 8.3 2.5 mM MgCl$_2$ 0.45% NonIdet P-40 |
| 5 | 200 mM NaCl 20 mM Tris-HCl pH 7.5 5 mM EDTA 70% Ethanol | 10 mM Tris-HCl pH 7.5 1 mM EDTA | 200 mM NaCl 20 mM Tris-HCl pH 7.5 5 mM EDTA 70% Ethanol |
| 6 | 10 mM Tris-HCl pH 7.5 1 mM EDTA | | 10 mM Tris-HCl pH 7.5 1 mM EDTA |
| 7 | Wizard DNA purification resin in 7 M Guanidine HCl | | Wizard DNA purification resin in 7 M Guanidine HCl |
| Upper Filter | 1 μm cellulose acetate | 1 μm cellulose acetate | Leukosorb type A or B |
| Lower Filter | 20 μm PTFE | 1 μm borosilicate glass | 1 μm borosilicate glass |

Example II
Purification Protocol for Plasmid DNA

The column for purifying plasmid DNA has two filters: upper 1 um filter 46 and lower 20 um filter 49. The material of the filter is chosen to resist the chemicals used during the process and to have appropriate flow characteristics to allow the process to occur as quickly as possible. A freshly grown culture of E.coli containing a plasmid to be purified is added to chamber 41, typically 1–5 ml. Addition could be made by means of removing the top or by direct addition via a tube (not shown). Positive pressure is then applied to chamber 41 by means of port 42. The bacteria are then filtered through filter 46 with the excess liquid passing to waste via conduit 47, filter 49 and valve 50. The liquid waste is monitored by flow sensor 51. Once all liquid has passed the flow sensor a dose of reagent 2 (TE/RNAase) is added to the top of chamber 41 via inlet 3, typically 30 ul. To effect mixing, chamber 8 is pressurised in short bursts via line 44 and pressure in chamber 41 is vented via port 42. This is done to ensure that all the cells caught on the filter are resuspended. A dose of reagent 3 (NaOH/SDS) is added to the top of chamber 41 via inlet 43, typically 300 ul. This is then mixed as described for reagent 2. A dose of reagent 4 (KAcetate) is added to the top of chamber 41 via inlet 43, typically 300 ul. This is then mixed as described for reagent 2. The resulting mixture is a cell free lysate of crude DNA with precipitated proteins. The cell free lysate of crude DNA is then transferred from chamber 46 to chamber 48 by addition of positive pressure via port 42, venting chamber 48 via line 44 and closing valve 50. A dose of reagent 7 (a DNA binding agent, e.g. silica resins, diatomaceous earth, affinity matrix) is added to chamber 48 via tube 55, typically 500 ul. The DNA binding agent is then mixed with the crude DNA by passing air into chamber 40 via line 45. The excess liquid is then removed from chamber 48 to waste. The DNA is retained on the DNA binding agent which will not pass through filter 49. A dose of reagent 5 (50% Ethanol/NaCl) is added to chamber 48 via line 45, typically 2000 ul and passed through filter 49 and removed directly to waste by means of pressurising chamber 48 with air from line 44. Air is continued to be passed through filter 49 for a period that allows the filter to dry sufficiently. The indexing mechanism 54 moves the collecting tube 52 so that it is in line with the exit tube from chamber 48. The DNA is then eluted from chamber 48 by the addition of, typically, 50 ul of reagent 6(TE) via lines 45 and expelled from chamber 48 by the addition of pulses of pressure via line 44.

In between liquid additions the lines are rinsed out with water (reagent 1) and via valve 68 (FIG. 6).

EXAMPLES III
Purification Protocol for Ml3 DNA

Different reagents are used to purify DNA from Ml3 but the essential elements of the apparatus are the same. The column for purifying single stranded Ml3 DNA has two filters: upper 1 um filter 46; and lower 1 um filter 49. The material of the filter is chosen to resist the chemicals used during the process and to have appropriate flow/binding characteristics to allow the process to occur as quickly as possible. A freshly grown culture of *E.coli* containing Ml3 to be purified is added to chamber 41, typically 1–5 ml. Positive pressure is then applied to chamber 41 by means of port 42. The bacteria are then filtered through filter 46 with the excess liquid containing Ml3 phage passing into chamber 48 via conduit 47. A dose of reagent 2 (Glacial acetic acid) is added to the top of chamber 41 via inlet 43, typically 20 ul. The phage are then filtered through filter 49 with the excess liquid passing to waste via valve 50. The liquid waste is monitored by flow sensor 51. Once all liquid has passed the flow sensor, a dose of reagent 3 (4M NaClO$_4$) is added to the top of chamber 48 via line 45, typically 1000 ul. The filter 49 is then washed with a dose of reagent 4 (70% EtOH), typically 1000 ul, and removed directly to waste by means of pressurising chamber 48 with air from line 44. Air is continued to be passed through filter 49 for a period that allows the filter to dry sufficiently. The indexing mechanism 54 moves the collecting tube 52 so that it is in line with the exit tube from chamber 48. The Ml3 DNA is then eluted from chamber 48 by the addition of, typically, 50 ul of reagent 5 (TE) via line 45 and expelled from chamber 48 by the addition of pulses of pressure via line 44.

EXAMPLES IV
Purification Protocol for Genomic DNA from Blood

The column for the purification of genomic DNA from blood has two filters: upper filter 46 is a Leukosorb type A or B (Pall Biosurport division); and lower filter 49 is a 20 um filter. The material of the upper filter was chosen so that it would retain nucleated cells while allowing denucleated red blood cells through. Freshly collected blood with EDTA as anti-coagulant was added to chamber 41 typically 1–10 ml. This could be done by means of removing the top or by direct addition via a tube (not shown).

Positive pressure is then applied to chamber 41 by means of inlet 42. The red blood cells are then filtered through filter 46 with the excess liquid passing to waste via conduit 47, filter 49 and valve 50. The liquid waste is monitored by flow sensor 51. Once all liquid has passed the flow sensor a dose of reagent 2 (PBS) is added to the top of chamber 41 via line 43, typically 2000 ul. To effect mixing chamber 48 is pressurised in short bursts via line 44 and chamber 41 is vented via inlet 42. This is done to ensure that cells caught on the filter are resuspended. A dose of reagent 3 (20TE) is added to the top of chamber 41 via line 43, typically 2000 ul, to lyse any remaining red blood cells. This is then mixed as described for reagent 2. The white blood cells are then lysed with a dose of reagent 4 (lysis buffer) which is added to the top of chamber 41 via line 43, typically 500 ul. This is then mixed as described for reagent 1. The resulting mixture is a cell free lysate of crude DNA. This is then transferred from chamber 41 to chamber 48 by addition of positive pressure via port 42, venting chamber 48 via line 44 and closing valve 50. A dose of reagent 7 (a DNA binding agent, e.g. silica resins, diatomaceous earth, affinity matrix) is added to chamber 48 via tube 55, typically 500 ul. The DNA binding agent is then mixed with the crude DNA by passing air into chamber 48 via line 45. The excess liquid is then removed from chamber 48 to waste. The DNA is retained on the DNA binding agent which will not pass through filter 49. A dose of reagent 5 (50% Ethanol/NaCl) is added to chamber 48 via line 45, typically 2000 ul and passed through filter 49 and removed direclty to waste by means of pressurising chamber 48 with air from line 44. Air is continued to be passed through filter 49 for a period that allows the filter to dry sufficiently. The indexing mechanism moves the collecting tube 52 so that it is in line with the exit tube from chamber 48. The DNA is then eluted from chamber 48 by the addition of pulses of pressure via line 44. In between liquid additions the lines are rinsed out with water (reagent 1) via valve 68 (FIG. 6).

| Key to FIG. 6 | | |
|---|---|---|
| Symbols | | Numbers |
| | 2 way valve normally closed | 61, 62, 63, 64, 65, 66, 75 |
| | 2 way valve normally open | 69, 73 |
| | 3 way valve for liquid | 68, 80 |
| | 3 way valve for air | 67, 70, 71, 76, 77, 78, 79 |
| | 3 way pinch valve for air | 74 |
| | 2 way pinch valve normally open | 79 |
| | Liquid column detector | LCD1 |
| | Non return valve | NRV1, NRV2, NRV3, NRV4 |
| | Reagent bottles | R1, R2, R3, R4, R5, R6, R8 |
| | Reagent bottle | R7 |
| | Flow constrictor 0.3 mm i.d. | C1, C2, C3 |
| | Compressed air cylinder actuator | |
| | Air filter 0.2 μm | |
| | Air filter 5 μm | |

-continued

Key to FIG. 6

| Symbols | Numbers |
|---|---|
| | Pressure regulator with gauge |
| | Variable flow control |
| | Compressed air source |
| | Air vent |
| | Line to waste |
| | Tube, inside diameter 3 mm |
| | Tube, inside diameter 0.8 mm |
| | Tube, inside diameter 0.5 mm |

What is claimed is:

1. A method for continuous purification of nucleic acid from cells, which method comprises the following steps:

(1) applying a crude cell suspension from a first chamber, delimited by a wall, to a filter to separate the cells from medium and resuspending the cells in the first chamber to form a cell suspension;

(2) lysing the cell suspension in the first chamber to form a cell lysate containing nucleic acid;

(3) applying the cell lysate to the filter to remove unwanted cells and cell debris;

(4) contacting the filtered lysate with a solid phase matrix retained in or downstream of a second chamber, delimited by a wall, under conditions to bind the nucleic acid to the matrix;

(5) separating the resultant filtered lysate from the matrix; and (6) applying liquid to the matrix through solution delivery means communicating with the second chamber so as to elute the nucleic acid from the matrix through an outlet which is provided downstream of the matrix;

wherein the walls of the first and second chambers are continuous with one another;

wherein the step of resuspending the cells in the first chamber comprises adding resuspension buffer to the cells and producing a pressure difference across the filter to resuspend the cells retained by the filter so as to form the cell suspension; and wherein the method does not include a centrifugation step.

2. The method according to claim 1, wherein the nucleic acid is DNA.

3. The method according to claim 2, wherein the DNA is plasmid DNA.

4. The method according to claim 2, wherein the cells are blood cells.

5. The method according to claim 4, wherein the crude cell suspension comprises blood.

6. The method according to claim 1, wherein the solid phase matrix is retained by a second filter.

7. The method according to claim 1, wherein the matrix and bound nucleic acid are dried by passage of air prior to elution.

8. The method according to claim 1, which further comprises the step of washing the matrix after binding the nucleic acid and before step (5) to remove contaminants before eluting the nucleic acid from the matrix.

9. The method according to claim 1, wherein each filter has a pore size in the range 0.2 to 50 microns.

10. The method according to claim 1, wherein the step of contacting the filtered lysate with the solid phase matrix comprises adding a suspension of the solid phase matrix to the filtered lysate.

11. The method according to claim 1, wherein the solid phase matrix comprises an ion exchange material.

12. The method according to claim 11, wherein the ion exchange material is an anion exchange material.

13. The method according to claim 1, wherein the nucleic acid is kept in solution when not bound to the solid phase matrix.

14. An apparatus for the continuous purification of a target compound from a crude cell suspension comprising:

a first chamber for receiving the crude cell suspension, for receiving a cell suspension of re-suspended cells, and for receiving cell lysate formed from lysed cell suspension;

a filter downstream of the first chamber for separating cells from medium and retaining unlysed cells and cell debris;

a second chamber for receiving filtered lysate downstream of the filter;

means for retaining a solid phase matrix to bind the target compound provided in or downstream of the second chamber;

solution delivery means communicating with the second chamber for eluting the target compound from the matrix;

an outlet for delivering the purified target compound provided downstream of the means for retaining the solid phase matrix; and fluid delivery means having an outlet which is positioned to communicate with liquid when present in the second chamber;

wherein the walls of the first and second chambers are continuous with one another; and wherein means are provided for producing a pressure difference across the filter to re-suspend cells retained by the filter and form the cell suspension.

15. The apparatus according to claim 14, wherein the first chamber communicates with further means for delivering solutions thereto.

16. The apparatus according to claim 15, wherein the means for delivering solutions is driven by a pneumatic fluid delivery system using continuous pressure.

17. The apparatus according to claim 14, further comprising first pressurization means for providing a positive pressure at the upstream end of the filter relative to the downstream end thereof.

18. The apparatus according to claim 17, wherein the first pressurization means is driven by a pneumatic fluid delivery system using continuous pressure.

19. The apparatus according to claims claim 14, wherein the means for retaining the solid phase matrix comprises a barrier to the solid phase matrix, which barrier is situated between at least a part of the second chamber and the outlet.

20. The apparatus according to claim 19, further comprising second pressurization means for providing a positive pressure at the upstream end of the barrier relative to the downstream end thereof.

21. The apparatus according to claim 14, wherein the second chamber communicates with means for delivering thereto a suspension the solid phase matrix.

22. The apparatus according to claim 21, wherein the means for delivering suspensions is driven by a pneumatic fluid delivery system using continuous pressure.

23. The apparatus according to claim 14, wherein a conduit is provided to transmit the filtrate from the filter to a collection point in the second chamber.

24. The apparatus according to claim 14, wherein each means for delivering solutions and, when present, the means for delivering suspensions and the pressurization means are driven by a pneumatic fluid delivery system using continuous pressure.

25. The apparatus according to claim 14, which further comprises control means for coordinating delivery of solutions, suspensions and pressure.

26. The apparatus according to claim 14, wherein the means for producing a pressure difference across the filter comprise a fluid line to pressurize the second chamber.

27. The apparatus according to claim 14, wherein the means for retaining a solid phase matrix comprises a second filter.

28. The apparatus according to 14, wherein means are provided for drying the matrix by air.

29. The apparatus according to claim 14, which further comprises a three-way valve downstream of the second chamber and upstream of the outlet for controlling elution from the apparatus.

* * * * *